United States Patent [19]

Gitzel et al.

[11] Patent Number: 5,053,537

[45] Date of Patent: Oct. 1, 1991

[54] AMMONIUM AND IMINIUM COMPOUNDS

[75] Inventors: Jörg Gitzel, Hattersheim am Main; Hans-Tobias Macholdt, Darmstadt; Frank Wehowsky, Niedernhausen; Günther Prossel, Burgkirchen, all of Fed. Rep. of Germany

[73] Assignee: Hoechst Aktiengesellschaft, Frankfurt am Main

[21] Appl. No.: 430,740

[22] Filed: Nov. 2, 1989

[30] Foreign Application Priority Data

Nov. 3, 1988 [DE] Fed. Rep. of Germany ...... 3837344
Jan. 17, 1989 [DE] Fed. Rep. of Germany ...... 3901153

[51] Int. Cl.$^5$ .............................................. C07F 5/02
[52] U.S. Cl. .......................................... 564/8; 546/13; 546/182; 546/347; 544/229
[58] Field of Search ............... 564/8, 281, 282, 288

[56] References Cited

U.S. PATENT DOCUMENTS 4,623,479 11/1986 Kucharska et al. .................. 564/8

Primary Examiner—Alan L. Rotman

[57] ABSTRACT

Ammonium compounds of the formula (I)

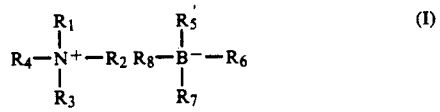

in which at least one of the radicals $R_1$ to $R_4$ denotes a fluorine-containing alkyl radical having 4 to 30 carbon atoms and not more than three of the radicals $R_1$ to $R_4$ independently of one another denote hydrogen atoms or alkyl or hydroxyalkyl radicals having 1 to 30 carbon atoms, and $R_5$ to $R_8$ denote aryl, alkylaryl or halogenoaryl radicals or fluorine atoms, and iminium compounds of the formula (II)

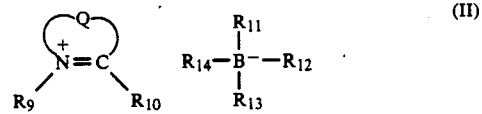

in which Q, together with the constituent

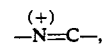

forms a ring system having 4 to 17 carbon atoms, which can be interrupted by 1 to 4 hetero atoms and contain 2 to 9 double bonds, and which can be substituted by fluorine, chlorine, bromine or iodine atoms or alkyl ($C_1$–$C_6$), alkoxy ($C_1$–$C_6$), nitro or amino groups, $R_9$ denotes a fluorine-containing alkyl ($C_1$–$C_{30}$) radical, $R_{10}$ denotes a hydrogen, fluorine, chlorine, bromine or iodine atom or an alkyl($C_1$–$C_6$), alkoxy ($C_1$–$C_6$), nitro or amino group and the radicals $R_{11}$ to $R_{14}$ denote aryl radicals, alkylaryl radicals, halogenoaryl radicals or fluorine atoms, and mixtures of these compounds and processes for their preparation.

13 Claims, No Drawings

AMMONIUM AND IMINIUM COMPOUNDS

The present invention relates to novel ammonium and iminium compounds and processes for their preparation.

The present invention specifically relates to novel ammonium compounds of the general formula (I)

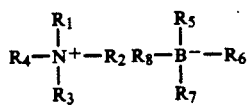  (I)

in which at least one of the radicals $R_1$ to $R_4$ denotes a straight-chain fluorine-containing unsaturated and/or saturated alkyl radical having 4 to 30 carbon atoms and not more than three of the radicals $R_1$ to $R_4$ independently of one another denote hydrogen atoms or straight-chain or branched alkyl or hydroxyalkyl radicals having 1 to 30 carbon atoms, and $R_5$ to $R_8$ denote aryl radicals, such as, for example, phenyl or naphthyl radicals, and furthermore alkylaryl radicals, such as, for example, the toluyl radical, halogenoaryl radicals, such as, for example, fluorophenyl or chlorophenyl radicals, or fluorine atoms, and to mixtures of these compounds, and iminium compounds of the general formula (II)

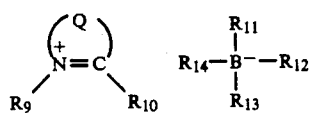  (II)

in which Q, together with the constituent

forms a mono- or polynuclear ring system having 4 to 17 carbon atoms, which can additionally be interrupted by 1 to 4 hetero atoms, such as, for example, nitrogen, oxygen or sulfur atoms, and contain 2 to 9 double bonds, and which can be substituted in any desired position by fluorine, chlorine, bromine or iodine atoms or alkyl($C_1$-$C_6$), alkoxy($C_1$-$C_6$), nitro or amino groups, $R_9$ denotes a fluorine-containing alkyl($C_1$-$C_{30}$) radical, $R_{10}$ denotes a hydrogen, fluorine, chlorine, bromine or iodine atom or an alkyl($C_1$-$C_6$), alkoxy($C_1$-$C_6$), nitro or amino group and the radicals $R_{11}$ to $R_{14}$ denote aryl radicals, such as, for example, phenyl or naphthyl radicals, alkylaryl radicals, such as, for example, the toluyl radical, halogenoaryl radicals, such as, for example, fluorophenyl or chlorophenyl radicals, or fluorine atoms, and to mixtures of these compounds.

The invention particularly relates to those compounds of the abovementioned general formula (I) in which at least one of the radicals $R_1$ to $R_4$ denotes a straight-chain fluorine-containing unsaturated and/or saturated alkyl radical having 4 to 14C atoms and not more than three of the radicals $R_1$ to $R_4$ independently of one another denote straight-chain or branched alkyl(-$C_1$-$C_4$) or hydroxyalkyl($C_1$-$C_4$) radicals, and $R_5$ to $R_8$ denote phenyl, naphthyl, p-chlorophenyl or p-toluyl radicals or fluorine atoms, and to compounds of the general formula (II) mentioned, in which Q, together with the constituent

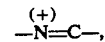

forms a mono- or polynuclear ring system having 4 to 10 carbon atoms, which can additionally be interrupted by 1 to 4 hetero atoms, such as, for example, nitrogen, oxygen or sulfur atoms, and contain 2 to 5 double bonds and which can be substituted in any desired position by fluorine, chlorine, bromine or iodine atoms or alkyl(-$C_1$-$C_6$), alkoxy($C_1$-$C_6$), nitro or amino groups, $R_9$ denotes a fluorine-containing alkyl($C_4$-$C_{14}$) radical, $R_{10}$ denotes a hydrogen, fluorine, chlorine, bromine or iodine atom or an alkyl($C_1$-$C_6$), alkoxy($C_1$-$C_6$), nitro or amino group and the radicals $R_5$ to $R_8$ and $R_{11}$ to $R_{14}$ denote phenyl, p-chlorophenyl, p-toluyl or naphthyl radicals or fluorine atoms, and to mixtures of these compounds.

The invention especially relates to compounds of the abovementioned general formula (I) in which at least one of the radicals $R_1$ to $R_4$ denotes the group —$CH_2$—$CH$=$CF$—$Rf$ ($Rf$=$C_5F_{11}$—$C_{11}F_{23}$), the group —$CH_2$—$CH$=$CF$—$C_nF_{2n+1}$, where n=5, 7 or 9, or the group —$CH_2$—$CH$=$CF$—$C_7F_{15}$, and not more than three of the radicals $R_1$ to $R_4$ independently of one another denote a methyl, ethyl, butyl or hydroxyethyl group, and to compounds of the abovementioned general formula (II) in which Q, together with the constituent

forms a pyridine, pyrazine or quinoline ring system, $R_9$ denotes a $C_8F_{17}$—$CH_2$—$CH_2$— group, $R_{10}$ denotes a hydrogen atom and the radicals $R_5$ to $R_8$ and $R_{11}$ to $R_{14}$ denote phenyl, p-chlorophenyl, p-toluyl or naphthyl radicals or fluorine atoms, and to mixtures of these compounds.

The following may be mentioned as examples of individual compounds or mixtures of compounds of the general formulae (I) or (II):

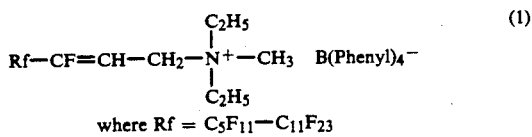  (1)

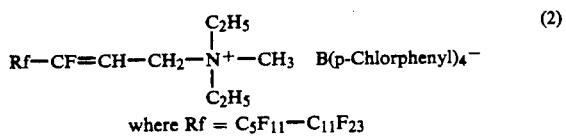  (2)

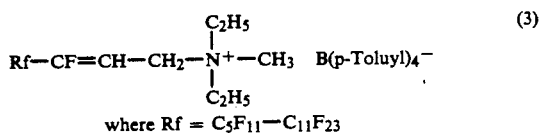  (3)

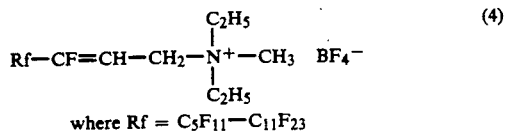  (4)

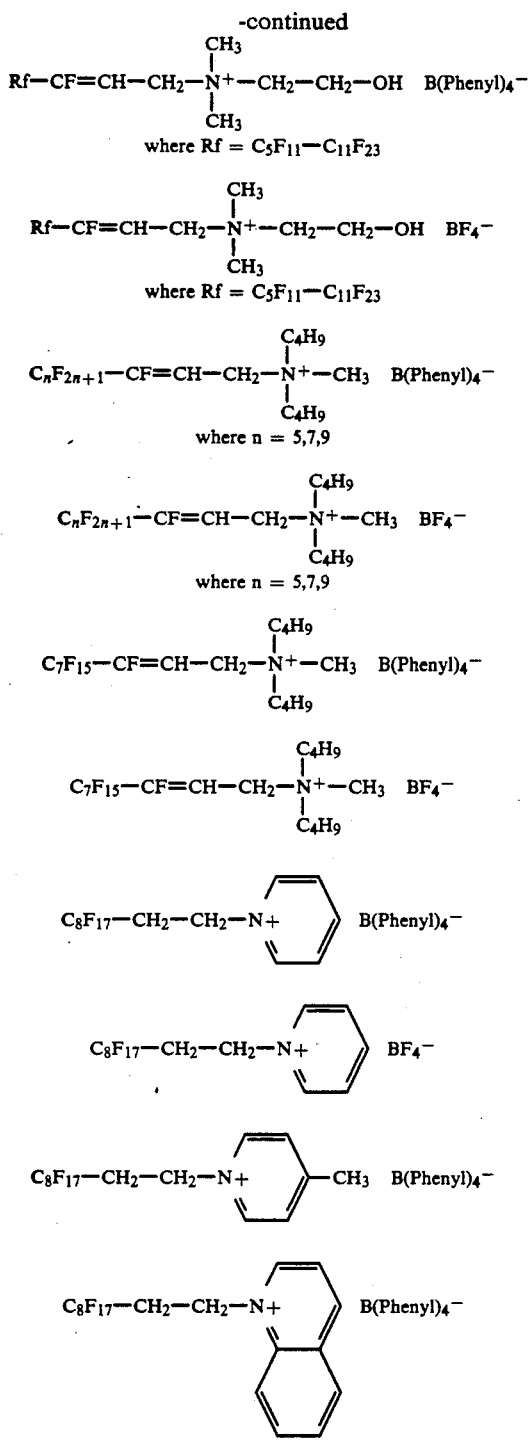

(5) $Rf-CF=CH-CH_2-\overset{\underset{|}{CH_3}}{\underset{|}{N^+}}-CH_2-CH_2-OH \quad B(Phenyl)_4^-$ where $Rf = C_5F_{11}-C_{11}F_{23}$ (6) $Rf-CF=CH-CH_2-\overset{\underset{|}{CH_3}}{\underset{|}{N^+}}-CH_2-CH_2-OH \quad BF_4^-$ where $Rf = C_5F_{11}-C_{11}F_{23}$ (7) $C_nF_{2n+1}-CF=CH-CH_2-\overset{\underset{|}{C_4H_9}}{\underset{|}{N^+}}-CH_3 \quad B(Phenyl)_4^-$ where $n = 5,7,9$ (8) $C_nF_{2n+1}-CF=CH-CH_2-\overset{\underset{|}{C_4H_9}}{\underset{|}{N^+}}-CH_3 \quad BF_4^-$ where $n = 5,7,9$ (9) $C_7F_{15}-CF=CH-CH_2-\overset{\underset{|}{C_4H_9}}{\underset{|}{N^+}}-CH_3 \quad B(Phenyl)_4^-$

(10) $C_7F_{15}-CF=CH-CH_2-\overset{\underset{|}{C_4H_9}}{\underset{|}{N^+}}-CH_3 \quad BF_4^-$ (11)–(14) pyridinium/quinolinium compounds with $C_8F_{17}-CH_2-CH_2-N^+$ The ammonium or iminium compounds and mixtures of ammonium or iminium compounds of the general formulae (I) or (II) mentioned can be prepared by reacting the ammonium compounds and mixtures of ammonium compounds of the general formula (III)

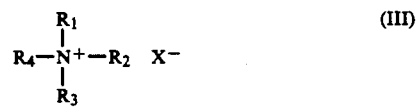

in which at least one of the radicals $R_1$ to $R_4$ denotes a straight-chain fluorine-containing unsaturated and/or saturated alkyl radical having 4 to 30 carbon atoms and not more than three of the radicals $R_1$ to $R_4$ independently of one another denote hydrogen atoms or straight-chain or branched alkyl or hydroxyalkyl radicals having 1 to 30 carbon atoms, and $X^-$ denotes a halogen anion, for example a chlorine, bromine or iodine anion, or a methylsulfate anion, and by reacting iminium compounds or mixtures of iminium compounds of the general formula (IV)

in which Q, together with the constituent $$\overset{(+)}{-N=C-},$$

forms a mono- or polynuclear ring system having 4 to 17 carbon atoms, which can additionally be interrupted by 1 to 4 hetero atoms, preferably nitrogen, oxygen or sulfur atoms, and contain 2 to 9 double bonds, and which can be substituted in any desired position by fluorine, chlorine, bromine or iodine atoms or an alkyl($C_1$-$C_6$), alkoxy($C_1$-$C_6$), nitro or amino group, $R_9$ denotes a fluorine-containing alkyl($C_1$-$C_{30}$) radical, $R_{10}$ denotes a hydrogen, fluorine, chlorine, bromine or iodine atom or an alkyl($C_1$-$C_6$), alkoxy($C_1$-$C_6$), nitro or amino group and $Y^-$ denotes a halogen anion, for example a chlorine, bromine or iodine anion, or a methylsulfate anion (the synthesis of the compounds of the general formulae III and IV mentioned is described in U.S. Pat. No. 3,535,381, German Offenlegungsschrift 1,922,277, German Offenlegungsschrift 2,244,297 and German Offenlegungsschrift 3,306,933), with a borate salt in water or mixtures of water and organic solvent, such as, for example, isopropanol, isobutanol or methyl isobutyl ketone, at temperatures from about 20° C. to about 90° C., preferably from about 50° C. to about 80° C.

The compounds and compound mixtures of the general formulae (I) and (II) are obtained in a good yield and purity by this process and can be isolated directly from the reaction medium by filtration.

Thus, for example, the above compounds of the formulae (1) to (14) are prepared by reacting the starting compounds (15) to (21) below

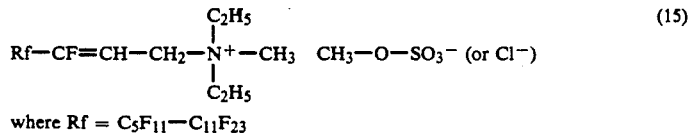

(15) $Rf-CF=CH-CH_2-\overset{\underset{|}{C_2H_5}}{\underset{|}{N^+}}-CH_3 \quad CH_3-O-SO_3^- \text{ (or Cl}^-\text{)}$ where $Rf = C_5F_{11}-C_{11}F_{23}$

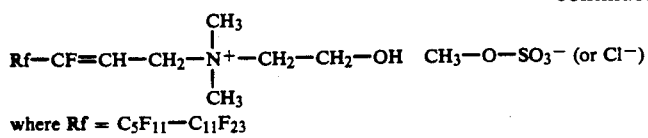  (16)

where Rf = $C_5F_{11}-C_{11}F_{23}$

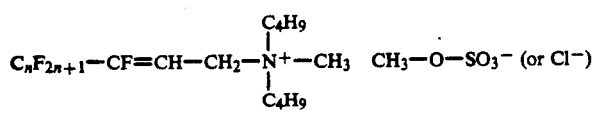  (17)

where n = 5,7,9

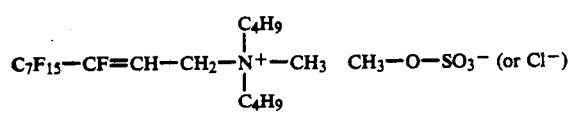  (18)

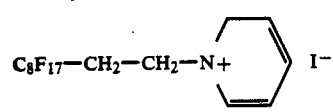  (19)

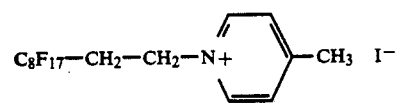  (20)

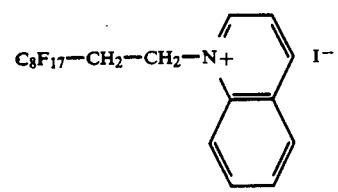  (21)

with sodium tetraphenylborate, sodium tetra-p-chlorophenylborate, sodium tetra-p-toluylborate or sodium tetrafluoroborate see the following Preparation Examples 1 to 6). Sodium tetra-p-chlorophenylborate and sodium tetra-p-toluylborate were prepared in accordance with the instructions of H. Holzapfel and C. Richter, J. Prakt. Chem. 26 (1964), 15–23. The ammonium and iminium compounds according to the invention are outstandingly suitable for use as charge control agents in electrophotographic toners and developers for electrophotographic recording processes.

The preparation examples below serve to illustrate the invention without limiting it to these.

PREPARATION EXAMPLE 1

160 ml of water are added to 40 ml of a 0.5 molar aqueous solution (0.020 mol) of the compound of the above-mentioned formula (15) (molecular weight 672) and 22 ml of a 1.0M aqueous solution of sodium tetraphenylborate (0.022 mol) are then added dropwise over a period of 15 to 20 minutes, while stirring vigorously. The mixture is made up to 500 ml with water and heated to 50° C. and the thick white precipitate is filtered off hot with suction. The product is washed thoroughly with water and dried at 50° C. in a circulating air cabinet.

| Yield | 16.9 g (96.0% of theory) of the compound (1) |
|---|---|
| Molecular weight | 880 |
| Melting point | 154–156° C. |
| Elemental analysis | calculated 4.1% H, 1.6% N, 1.2% B found 4.1% H, 1.6% N, 1.1% B, 0.05% water |
| 1H-NMR (in DMSO-d6) | 1.20 (triplet, 6 methyl-H), 2.97 (singlet, 3 methyl-H), 3.30 (quartet, 4 methylene-H), 4.25 (doublet, 2 allyl-H), 6.61 (doublet of triplets, 1 vinyl-H), 7.01 (multiplet, 20 phenyl-H) ppm. |

PREPARATION EXAMPLE 2

The procedure was as described in Preparation Example 1, with the difference that sodium tetra-p-chlorophenylborate was used instead of sodium tetraphenylborate.

| Yield | 15.4 g (75.6% of theory) of the compound of the abovementioned formula (2) |
|---|---|
| Molecular weight | 1018 |
| Melting point | 63–64° C. |
| Elemental anaylsis | calculated 3.1% H, 1.4% N, 1.1% B, 13.9% Cl, found 3.4% H, 1.5% N, 1.1% B, 14.5% Cl, 0.07% H2O |
| 1H-NMR (in DMSO-d6) | 1.23 (triplet, 6 methyl-H), 3.01 (singlet, 3 methyl-H), 3.36 (quartet, 4 methylene-H), 4.28 (doublet, 2 allyl-H), 6.63 (doublet of triplets, 1 vinyl-H), 7.04 (multiplet, 16 p-chlorophenyl-H) ppm. |

PREPARATION EXAMPLE 3

The procedure was as described in Preparation Example 1, with the difference that sodium tetra-p-toluylborate was employed instead of sodium tetraphenylborate and the solvent was replaced by isopropanol/water (1:1 parts by volume).

| Yield | 11.5 g (61.2% of theory) of the compound of the abovementioned formula (3) |
|---|---|
| Molecular weight | 936 |
| Melting point | 151–152° C. |
| Elemental analysis | calculated 4.7% H, 1.5% N, 1.2% B found 5.0% H, 1.9% N, 1.2% B, 0.07% $H_2O$ |
| 1H-NMR (in DMSO-d6) | 1.21 (triplet, 6 methyl-H), 2.15 (singlet, 3 toluylmethyl-H), 2.97 (singlet, 3 methyl-H), 3.33 (quartet, 4 methylene-H), 4.23 (doublet, 2 allyl-H), 6.60 (partly overlapped doublet of triplets, 1 vinyl-H), 6.88 (multiplet, 16 p-toluyl-H) ppm. |

PREPARATION EXAMPLE 4

The procedure was as described in Preparation Example 1, with the difference that sodium tetrafluoroborate was employed instead of sodium tetraphenylborate.

| Yield | 12.3 g (95.0% of theory) of the compound of the abovementioned formula (4) |
|---|---|
| Molecular weight | 648 |
| Melting point | 202° C. |
| Elemental analysis | calculated 2.5% H, 2.2% N, 1.7% B found 2.7% H, 2.3% N, 1.8% B, 0.5% water |
| 1H-NMR (in DMSO-d6) | 1.24 (triplet, 6 methyl-H), 3.02 (singlet, 3 methyl-H), 3.37 (quartet, 4 ethyl-H), 4.28 (doublet, 2 allyl-H), 6.63 (doublet of triplets, 1 vinyl-H), ppm. |

PREPARATION EXAMPLE 5

7.8 g (0.012 mol) of the compound (19) are dissolved in 200 ml of hot isobutanol. 100 ml of water are then added and 4.1 g (0.012 mol) of sodium tetraphenylborate are then slowly added, while stirring. The mixture is stirred vigorously for 1 hour and the product is then filtered off with suction, washed with isobutanol/water (1:1 parts by volume) and then washed with water and dried at 50° C. in vacuo.

| Yield | 9.1 g (89.7% of theory) of the compound of the abovementioned formula (11) |
|---|---|
| Molecular weight | 845 |
| Melting point | 163° C. |
| Elemental analysis | calculated 55.4% C, 3.5% H, 1.7% N, 1.3% B, 38.2% F found 55.2% C, 3.3% H, 1.6% N, 1.2% B, 36.8% F, 0.19% water |
| 1H-NMR (in DMSO-d6) | 3.25 (multiplet, 2 methylene-H), 4.97 (triplet, 2 methylene-H), 7.00 (multiplet, 20 phenyl-H), 8.59 (multiplet, 5 pyridyl-H), ppm. |

PREPARATION EXAMPLE 6

11.1 g (0.017 mol) of the compound of the abovementioned formula (19) are dissolved in 400 ml of hot water, and 1.9 g (0.017 mol) of sodium tetrafluoroborate are then slowly added, while stirring. The mixture is stirred vigorously for 1 hour, the product is filtered off hot with suction, washed with hot water and dried at 50° C. in vacuo.

| Yield | 8.7 g (83.5% of theory) of the compound of the abovementioned formula (12) |
|---|---|
| Molecular weight | 613 |
| Melting point | 169° C. |
| Elemental analysis | calculated 29.4% C, 1.5% H, 2.3% N, 1.8% B found 29.5% C, 1.6% H, 2.4% N, 1.5% B, 0.06% $H_2O$ |
| 1H-NMR (in DMSO-d6) | 3.21 (multiplet, 2 methylene-H), 5.03 (triplet, 2 methylene-H), 8.64 (multiplet, 5 pyridyl-H) ppm. |

The individual compounds and compound mixtures of the abovementioned formulae (5) to (10) and (13) and (14) were obtained analogously.

We claim:

1. An ammonium compound of the formula (I)

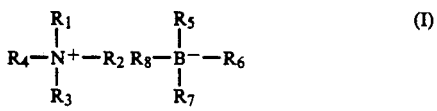

in which at least one of the radicals $R_1$ to $R_4$ denotes a straight-chain fluorine-containing unsaturated and/or saturated alkyl radical having 4 to 30 carbon atoms and not more than three of the radicals $R_1$ to $R_4$ independently of one another denote hydrogen atoms or straight-chain or branched alkyl or hydroxyalkyl radicals having 1 to 30 carbon atoms, and $R_5$ to $R_6$ denote phenyl, p-chlorophenyl, p-fluorophenyl, p-toluyl, or naphthyl radicals or fluorine atoms.

2. A compound of the formula (I) as claimed in claim 1, in which at least one of the radicals $R_1$ to $R_4$ denotes a straight-chain fluorine-containing unsaturated and/or saturated alkyl radical having 4 to 14 carbon atoms and not more than three of the radicals $R_1$ to $R_4$ independently of one another denote straight-chain or branched alkyl($C_1$-$C_4$) or hydroxyalkyl($C_1$-$C_4$) radicals, and $R_5$ to $R_8$ denote phenyl, naphthyl, p-chlorophenyl, p-toluyl radicals or fluorine atoms.

3. A compound of the formula (I) as claimed in claim 1, in which at least one of the radicals $R_1$ to $R_4$ denotes the group —$CH_2$—CH=CF—Rf (Rf=$C_5F_{11}$—$C_{11}F_{23}$), the group —$CH_2$—CH=CF—$C_nF_{2n+1}$, where n=5, 7 or 9, or the group —$CH_2$—CH=CF—$C_7F_{15}$, and not more than three of the radicals $R_1$ to $R_4$ independently of one another denote a methyl, ethyl, butyl or hydroxyethyl group.

4. A compound or mixture of compounds of the formula

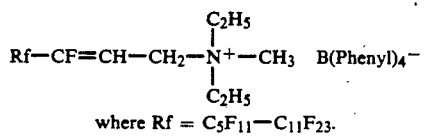

where Rf = $C_5F_{11}$—$C_{11}F_{23}$.

5. A compound or mixture of compounds of the formula

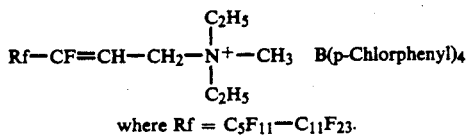
6. A compound or mixture of compounds of the formula
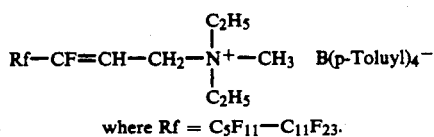
7. A compound or mixture of compounds of the formula
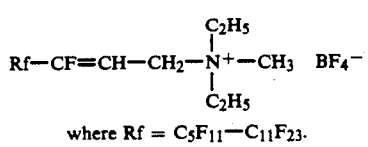
8. A compound or mixture of compounds of the formula
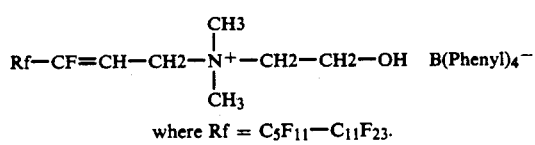
9. A compound or mixture of compounds of the formula
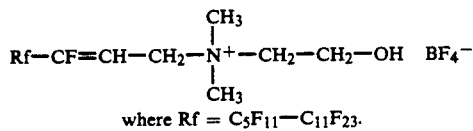
10. A compound or mixture of compounds of the formula
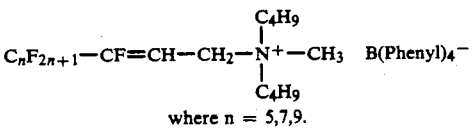
11. A compound or mixture of compounds of the formula
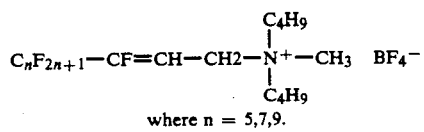
12. The compound of the formula
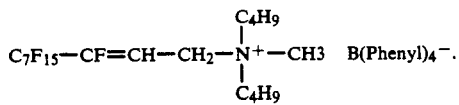
13. The compound of the formula
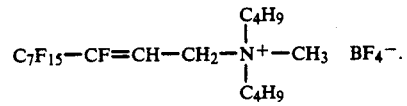
* * * * *